US011357410B2

(12) United States Patent
Banerjee et al.

(10) Patent No.: US 11,357,410 B2
(45) Date of Patent: Jun. 14, 2022

(54) MEASURING BLOOD PRESSURE

(71) Applicant: TATA CONSULTANCY SERVICES LIMITED, Mumbai (IN)

(72) Inventors: Rohan Banerjee, West Bengal (IN); Anirban Dutta Choudhury, West Bengal (IN); Aniruddha Sinha, West Bengal (IN)

(73) Assignee: TATA CONSULTANCY SERVICES LIMITED

( * ) Notice: Subject to any disclaimer, the term of this patent is extended or adjusted under 35 U.S.C. 154(b) by 1053 days.

(21) Appl. No.: 14/643,333

(22) Filed: Mar. 10, 2015

(65) Prior Publication Data

US 2016/0038044 A1 Feb. 11, 2016

(30) Foreign Application Priority Data

Aug. 11, 2014 (IN) .......................... 2593/MUM/2014

(51) Int. Cl.
*A61B 5/0205* (2006.01)
*A61B 5/021* (2006.01)
(Continued)

(52) U.S. Cl.
CPC ........ *A61B 5/0205* (2013.01); *A61B 5/02007* (2013.01); *A61B 5/02116* (2013.01); *A61B 5/02125* (2013.01); *A61B 5/02416* (2013.01); *A61B 5/7246* (2013.01); *A61B 5/7264* (2013.01); *A61B 5/7278* (2013.01); *G16H 50/50* (2018.01); *A61B 5/02241* (2013.01); *G16H 40/67* (2018.01); *G16H 50/20* (2018.01)

(58) Field of Classification Search
CPC .............. A61B 5/02125; A61B 5/7264; A61B 5/02116; A61B 5/02416; A61B 5/0205; A61B 5/7246; A61B 5/02007; A61B 5/7278; A61B 5/02241; G06F 19/3437; G06F 19/345; G06F 19/3418
See application file for complete search history.

(56) References Cited

U.S. PATENT DOCUMENTS 5,241,963 A * 9/1993 Shankar ............. A61B 5/02007
600/481
6,616,613 B1 9/2003 Goodman
(Continued)

OTHER PUBLICATIONS

Mathworks, "About Lookup Table Blocks", https://www.mathworks.com/help/simulink/ug/about-lookup-table-blocks.html, Online, accessed Mar. 13, 2020. (Year: 2013).*

(Continued)

*Primary Examiner* — Katherine L Fernandez
(74) *Attorney, Agent, or Firm* — Barnes & Thornburg LLP

(57) ABSTRACT

A method for measuring blood pressure of a subject is described herein. In an implementation, the method includes obtaining a plurality of photoplethysmogram (PPG) features associated with the subject. The method further includes ascertaining one or more latent parameters associated with the subject based on the plurality of PPG features and a reference model, wherein the reference model indicates a correlation between the plurality of PPG features and the one or more latent parameters. Further, blood pressure of the subject is determined based on the one or more latent parameters and the plurality of PPG features.

7 Claims, 3 Drawing Sheets

(51) Int. Cl.
*A61B 5/00* (2006.01)
*A61B 5/02* (2006.01)
*A61B 5/024* (2006.01)
*G16H 50/50* (2018.01)
*A61B 5/022* (2006.01)
*G16H 50/20* (2018.01)
*G16H 40/67* (2018.01)

(56) References Cited

U.S. PATENT DOCUMENTS

| | | | |
|---|---|---|---|
| 8,398,556 B2 | 3/2013 | Sethi et al. | |
| 2009/0163821 A1* | 6/2009 | Sola I Caros | A61B 5/02125 600/485 |
| 2010/0081940 A1* | 4/2010 | McKenna | A61B 5/02007 600/479 |
| 2010/0312115 A1* | 12/2010 | Dentinger | A61B 5/02116 600/450 |
| 2012/0136605 A1* | 5/2012 | Addison | A61B 5/02125 702/98 |
| 2015/0208923 A1* | 7/2015 | Aki | A61B 5/0084 600/479 |
| 2016/0022213 A1* | 1/2016 | Lee | A61B 5/6838 600/301 |

OTHER PUBLICATIONS

X.F. Teng and Y. T. Zhang, Continuous and noninvasive estimation of arterial blood pressure using a photoplethysmographic approach, in Engineering in Medicine and Biology Society, 2003. Proceedingsof the 25th Annual International Conference of the IEEE, 2003.

Francesco Lamonaca et al., Application of the artificial neural network for blood pressure evaluation with smartphones, in The 7th IEEE International Conference on Intelligent Data Acquisition and Advanced Computing Systems: Technology and Applications, 2013, pp. 408 412.

A. Mookerjee, A.M. Al-Jumaily, and A. Lowe, Individualised pressure propagation model for the elastic arteries, in World Congress on Medical Physics and Biomedical Engineering, 2010, pp. 586589.

* cited by examiner

MEASURING BLOOD PRESSURE

CROSS REFERENCE TO RELATED APPLICATIONS

This application claims priority to Indian Patent Application No. 2593/MUM/2014, filed 11 Aug. 2014. The disclosure set forth in the referenced application is incorporated herein by reference in its entirety.

TECHNICAL FIELD

The present subject matter relates, in general, to measurement of a physiological parameter of a subject and, particularly but not exclusively, to measuring blood pressure of a subject.

BACKGROUND

Measurement of various physiological parameters, such as blood pressure of an individual is typically performed in a clinical setting. For measuring blood pressure, several unobtrusive techniques have been developed. One such technique for measuring the blood pressure is photoplethysmography. Photoplethysmography is a non-intrusive technique for measuring blood pressure of an individual. In said technique, a photoplethysmogram (PPG), a type of an optical plethysomogram, associated with the individual may be analyzed for measuring the blood pressure of the individual.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
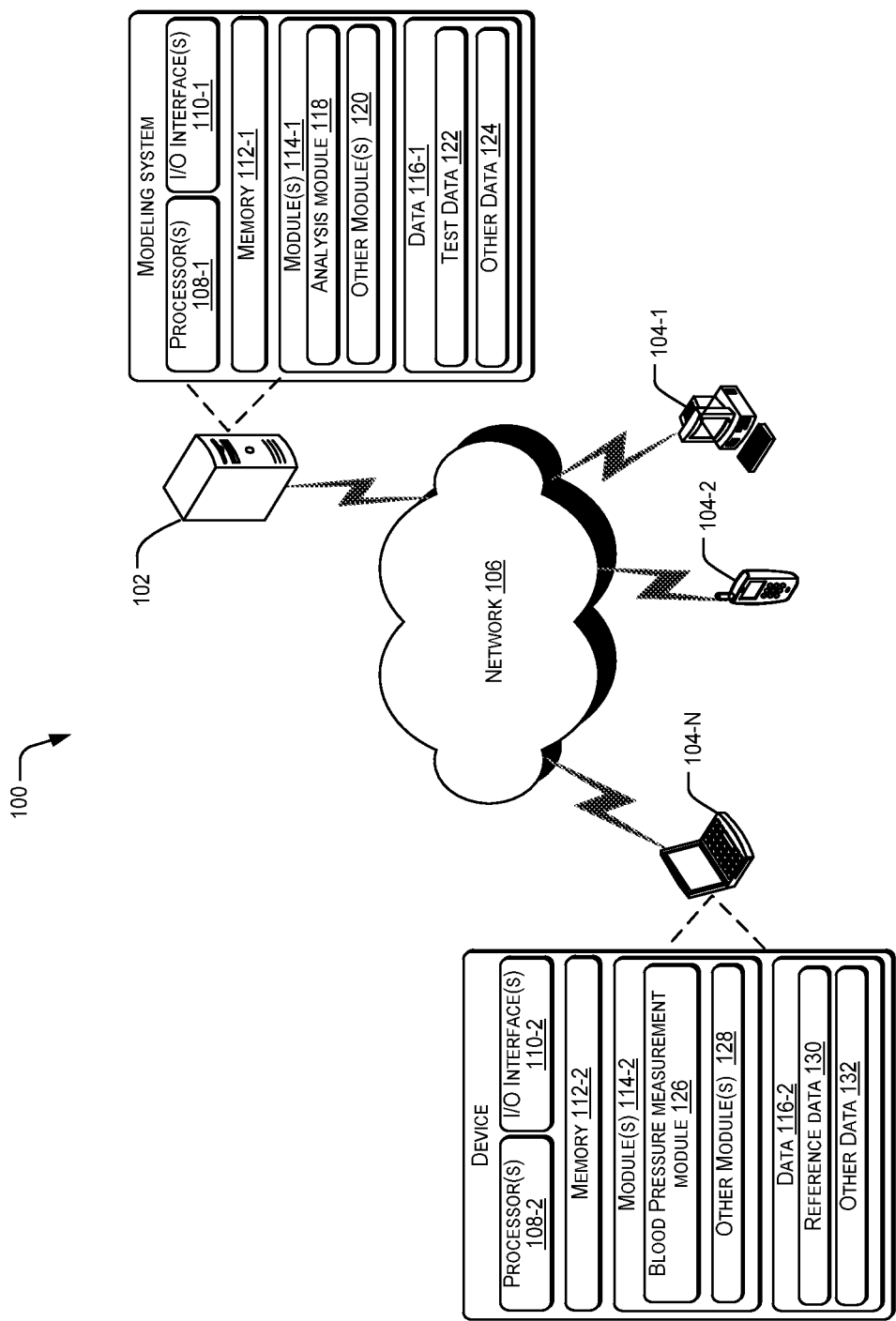
FIG. 1 illustrates a network environment for facilitating measurement of blood pressure of a subject, in accordance with an implementation of the present subject matter.

The present subject matter relates to measuring blood pressure of a subject, for example, an individual, based on a photoplethysmogram (PPG) associated with the subject.

Typically, an individual seeking to get his/her blood pressure measured may visit a medical clinic or a hospital. In such scenario, a physician or a trained medical technician measures the blood pressure of the individual with the help of medical instruments, such as a sphygmomanometer and a stethoscope. As may be gathered, in the aforementioned scenario, measurement of the blood pressure may only be performed by individuals having specific skill set suitable for efficiently using the medical instruments for measuring the blood pressure. Thus, periodical measurement of blood pressure may require regular visits to the medical clinic or hospital and may prove to be a cost intensive method for the individual.

In a conventional approach, an over the counter device implementing photoplethysmography may be used for measuring blood pressure. The photoplethysmography may be understood as a non-invasive optical technique for measuring physiological parameters, such as respiration rate, heart rate, and blood pressure of an individual. In such conventional approach, a PPG waveform associated with the individual may be obtained by processing a video of the individual or a video of a part of the body of the individual. Based on the PPG waveform and a predetermined statistical model, the blood pressure of the individual may then be determined. However, determination of the blood pressure based on the aforementioned approach may, at times, result in vague blood pressure measurement. For example, in a case where a statistical model based on a large dataset of blood pressure records is used for determining the blood pressure, accurate measurement of the blood pressure may be achieved. While, in a case where a statistical model based on a small dataset of blood pressure records is used, for example, in a case where low-budget devices are used for measuring the blood pressure, the blood pressure may be inaccurately determined. As may be gathered, the aforementioned approach based on the statistical model may not yield accurate measurement of the blood pressure. Further, the aforementioned approach does not take into account other physiological parameters of the individual. Thus, the approach may not provide for a true measurement of the blood pressure of the individual.

The present subject matter describes methods, system, and devices to measure blood pressure of a subject, for example, an individual. According to an aspect of the present subject matter, the blood pressure of the individual may be measured based on a PPG waveform associated with the subject and a reference model. In accordance with the present subject matter, the reference model may be based on one or more latent parameters, such as arterial compliance (R), peripheral resistance (C), blood flow from ventricles to artery ($T_0$), and cardiac output ($C_0$), associated with the individual. Measurement of the blood pressure of an individual based on the latent parameters of the individual results in higher degree of accuracy in the value of the blood pressure measured.

In an implementation, the reference model may be determined based on a sample dataset comprising physiological data associated with each of a plurality of test subjects. In an example, the physiological data, corresponding to a test subject, may include a ground truth value of blood pressure of the test subject and a PPG waveform associated with the subject. The ground truth value may be understood as a value of blood pressure measured using a conventional sphygmomanometer device. In said implementation, the PPG waveform may be processed for obtaining a plurality of PPG features. Examples of the PPG features may include, but are not limited to, systolic upstroke time period ($T_s$), diastolic time period ($T_d$), and a sum (B) of systolic width and diastolic width at predetermined intervals. Based on the PPG features and the ground truth value of the blood pressure, latent parameters associated with the test subject may be computed. As may be understood, the latent parameters for each of the test subjects are obtained. Latent parameters may be understood as parameters indicative of one or more physiological parameters of an individual. Thereafter, the reference model may be determined by correlating the latent parameters of the test subjects with the PPG features of the test subjects. The reference model may then be deployed in devices, for example, user equipments, such as mobile phones, laptops, and desktops, for measuring blood pressure of a subject in real time.

In an implementation, for measuring the blood pressure of the subject, a plurality of PPG features associated with the subject may be obtained. In an example, the PPG features may be obtained by processing a PPG waveform associated with the subject. Thereafter, based on the reference model and the PPG features, one or more latent parameters associated with the subject may be ascertained. As mentioned above, the reference model indicates a correlation between the PPG features and the latent parameters. Thus, a value of each of the latent parameters corresponding to the PPG features of the subject may be identified based on the reference model. Based on the latent parameters and the PPG features, the blood pressure of the subject may then be determined.

As will be clear from the foregoing description, latent parameters associated with a subject are taken into account while measuring the blood pressure of the subject. As a result, measurement of the blood pressure of a subject in accordance with the present subject matter is not totally dependent on a statistical model and involves latent parameters of the subject. Thus, high level of accuracy in measurement of blood pressure of a subject may be achieved.

These and other advantages of the present subject matter would be described in greater detail in conjunction with the following figures. While aspects of described systems and methods for measuring blood pressure can be implemented in any number of different computing systems, environments, and/or configurations, the embodiments are described in the context of the following device(s).

FIG. 1 illustrates a network environment 100 for facilitating measurement of blood pressure of a subject, in accordance with an embodiment of the present subject matter. The network environment 100 includes a modeling system 102 and a plurality of devices 104-1, 104-2, . . . , and 104-N, hereinafter collectively referred to as the devices 104 and individually referred to as the device 104. The modeling system 102 and the devices 104 may communicate with each other, through a network 106, according to an embodiment of the present subject matter.

In an implementation, the modeling system 102 may be implemented as one or more systems, such as a cloud server, a mainframe computer, a workstation, a multiprocessor system, a network computer, and a gateway server. In an example, the modeling system 102 may be provisioned to develop a reference model for facilitating measurement of blood pressure of a subject, for example, an individual, by using the devices 104. Based on the reference model, the blood pressure of the subject may be measured in real time. Examples of the device 104 may include, but are not limited to, a mobile phone, a smart phone, a personal digital assistant (PDA), a tablet, a laptop, a workstation computer, a server, and a personal computer.

The network 106 may be a wireless network, a wired network, or a combination thereof. The network 106 can also be an individual network or a collection of many such individual networks, interconnected with each other and functioning as a single large network, e.g., the Internet or an intranet. The network 106 can be implemented as one of the different types of networks, such as an intranet, local area network (LAN), wide area network (WAN), the internet, and such. Further, the network 106 may include network devices that may interact with the modeling system 102 and the devices 104 through communication links.

In one implementation, the modeling system 102 and the device 104 include processors 108-1 and 108-2, respectively. The processors 108-1 and 108-2, hereinafter collectively referred to as the processor 108, may be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory.

The functions of the various elements shown in the figure, including any functional blocks labeled as "processor(s)", may be provided through the use of dedicated hardware as well as hardware capable of executing software in association with appropriate software. When provided by a processor, the functions may be provided by a single dedicated processor, by a single shared processor, or by a plurality of individual processors, some of which may be shared.

Also, the modeling system 102 and the device 104 include I/O interface(s) 110-1 and 110-2, respectively. The I/O interfaces 110-1 and 110-2, collectively referred to as I/O interfaces 110 may include a variety of software and hardware interfaces that allow the modeling system 102 and the device 104 to interact with the network 106, or with each other. Further, the I/O interfaces 110 may enable the modeling system 102 and the device 104 to communicate with other communication and devices, such as web servers and external repositories. The modeling system 102 and the device 104 may further include memory 112-1 and 112-2, respectively, collectively referred to as memory 112. The memory 112-1 and 112-2 may be coupled to the processor 108-1, and the processor 108-2, respectively. The memory 112 may include any computer-readable medium known in the art including, for example, volatile memory (e.g., RAM), and/or non-volatile memory (e.g., EPROM, flash memory, etc.).

The modeling system 102 and the device 104 include modules 114-1, 114-2 and data 116-1, 116-2, respectively, collectively referred to as modules 114 and data 116, respectively. The modules 114 include routines, programs, objects, components, data structures, and the like, which perform particular tasks or implement particular abstract data types. The modules 114 further include modules that supplement applications on the modeling system 102 and the device 104, for example, modules of an operating system.

Further, the modules 114 can be implemented in hardware, instructions executed by a processing unit, or by a combination thereof. The processing unit can comprise a computer, a processor, such as the processor 108, a state machine, a logic array or any other suitable devices capable of processing instructions. The processing unit can be a general-purpose processor which executes instructions to cause the general-purpose processor to perform the required tasks, or the processing unit can be dedicated to perform the required functions.

In another aspect of the present subject matter, the modules 114 may be machine-readable instructions (software) which, when executed by a processor/processing unit, perform any of the described functionalities. The machine-readable instructions may be stored on an electronic memory device, hard disk, optical disk, or other machine-readable storage medium or non-transitory medium. In one implementation, the machine-readable instructions can be also be downloaded to the storage medium via a network connection. The data 116 serves, amongst other things, as a repository for storing data that may be fetched, processed, received, or generated by one or more of the modules 114.

In an implementation, the modules 114-1 of the modeling system 102 include an analysis module 118 and other module(s) 120. In said implementation, the data 116-1 of the modeling system 102 includes test data 122 and other data 124. The other module(s) 120 may include programs or coded instructions that supplement applications and functions, for example, programs in the operating system of the modeling system 102. The other data 124 comprise data corresponding to one or more other module(s) 120.

Similarly, in an implementation, the modules 114-2 of the device 104 include a blood pressure measurement module 126 and other module(s) 128. In said implementation, the data 116-2 of the device 104 includes reference data 130 and other data 132. The other module(s) 128 may include programs or coded instructions that supplement applications and functions, for example, programs in the operating system of the device 104. The other data 132 comprise data corresponding to one or more other module(s) 128.

In operation, the analysis module 118 may obtain a sample dataset for developing the reference model. The sample dataset may be understood as a collection of physiological data corresponding to each of a plurality of test subjects. In an example, the physiological data may include at least one ground truth value of blood pressure of a test subject and a PPG waveform associated with the test subject. In an implementation, the analysis module 118 may process the physiological data for obtaining a plurality of PPG features associated with the test subject. Examples of the PPG features may include, but are not limited to, a systolic upstroke time period ($T_s$), a diastolic time period ($T_d$), and a sum (B) of systolic width and diastolic width determined, based on the PPG waveform, at predetermined intervals. For example, the analysis module 118 may ascertain a time difference between a trough and a peak point immediate to the trough using known techniques. The time difference ascertained represents the systolic upstroke time period ($T_b$). Similarly, the analysis module 118 may then ascertain a time difference between a peak point and a trough immediate to the peak point using known techniques for identifying the diastolic time period ($T_d$). Similarly, the analysis module 118 may compute the sum (B) at predetermined intervals, say at thirty three percent and seventy five percent of the peak amplitude.

Thereafter, the analysis module 118 may compute one or more latent parameters associated with the test subject based on the PPG features and the at least one ground truth value. Examples of the latent parameters may include, but are not limited to, arterial compliance (R) and peripheral resistance (C), of the test subject. In an example, the analysis module 118 may compute the latent parameters using equations 1(a) and 1(b) illustrated below:

$$P_s = P_{ts}e^{-T_s/RC} + \frac{I_0 T_s C\pi R^2}{T_s^2 + C^2\pi^2 R^2}(1 + e^{-T_s/RC})$$  Equation 1(a)

where $P_s$, a ground truth value, is a maximum value of the blood pressure of the test subject. The maximum value of the blood pressure may also be referred to as systolic blood pressure. Further, $P_{ts}$ is the initial value of the systolic blood pressure, and $I_0$ is the blood flow from the ventricles to the arteries.

$$P_d = P_{td}e^{-T_d/RC}$$  Equation 1(b)

where $P_d$, a ground truth value, is a minimum value of the blood pressure of the test subject. The minimum value of the blood pressure may also be referred to as diastolic blood pressure. Further, $P_{td}$ is the initial value of the diastolic blood pressure.

In an example, the analysis module 118 may ascertain the equations 1(a) and 1(b) using a two-element Windkessel model. In said example, the analysis module 118 may replace the resistance of the two-element Windkessel model with arterial compliance and the capacitance with the peripheral resistance. Thereafter, the analysis module 118 may perform one or more linear regressions for obtaining the equations 1(a) and 1(b) and may store the same in test data 122.

Upon computing the values for the latent parameters of the test subject, the analysis module 118 may correlate the latent parameters of the test subject with the PPG features of the test subject. For example, for a set of values of PPG features, the corresponding latent parameters computed may be correlated with the set of PPG features. As may be understood, the analysis module 118 may correlate the latent parameters and the PPG features for each of the test subjects. Based on the correlation, the analysis module 118 may then determine the reference model. The reference model may then be used for measuring blood pressure of an individual in real time. For example, the reference model may be deployed in the devices 104 for facilitating measurement of blood pressure of a subject in real time.

In an implementation, the blood pressure measurement (BPM) module 126 may obtain a plurality of PPG features of a subject whose blood pressure is to be determined. In an example, the PPG features may be obtained from a user input provided by a user. For instance, values of the PPG features may be received from the user through an input device, such as a keyboard or a touch screen. In another example, the BPM module 126 may obtain the PPG features from a setup (not shown in figure) deployed for monitoring the PPG of the subject.

Upon obtaining the PPG features, the BPM module 126 may ascertain one or more latent parameters associated with the subject based on the PPG features and the reference model. The reference model may be stored in the reference data 130. As mentioned above, the reference model includes a plurality of correlations between latent parameters and PPG features. In order to ascertain the latent parameters, the BPM module 126 may compare the PPG features of the subject with the plurality of PPG features in the reference model. In a case where the BPM module 126 ascertains a successful match with any of the PPG features of the reference model, the BPM model 126 may ascertain the latent parameters value corresponding to the PPG features to be the latent parameters associated with the subject. Thereafter, the BPM module 126 may determine the blood pressure of the subject based on the latent parameters and the PPG features. In an example, the BPM module 126 may determine the blood pressure based on the equations 1(a) and 1(b) stated above.

Figure 2:
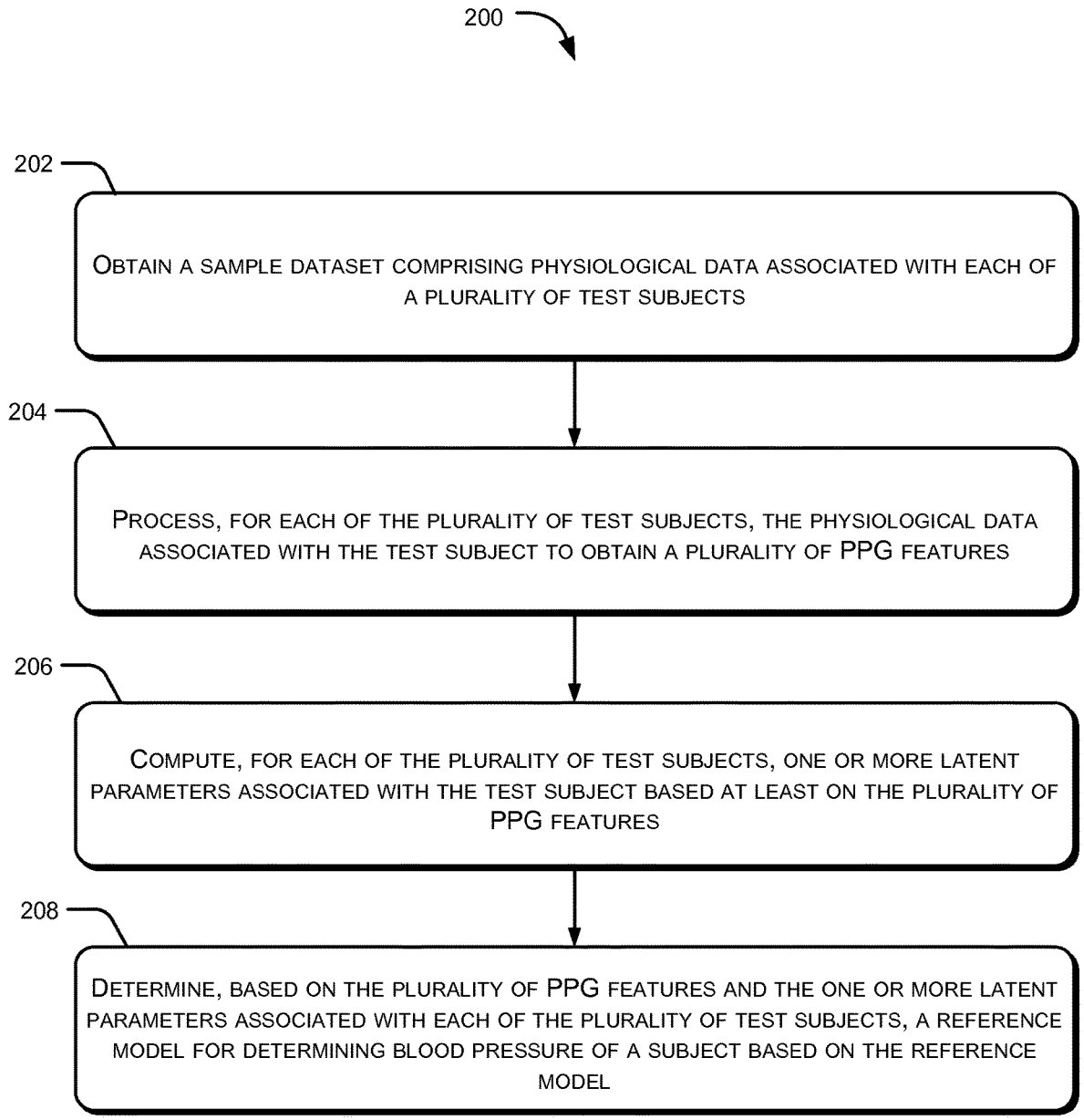
FIG. 2 illustrates a method for determining a reference model to measure blood pressure of a subject, in accordance with an implementation of the present subject matter.
Figure 3:
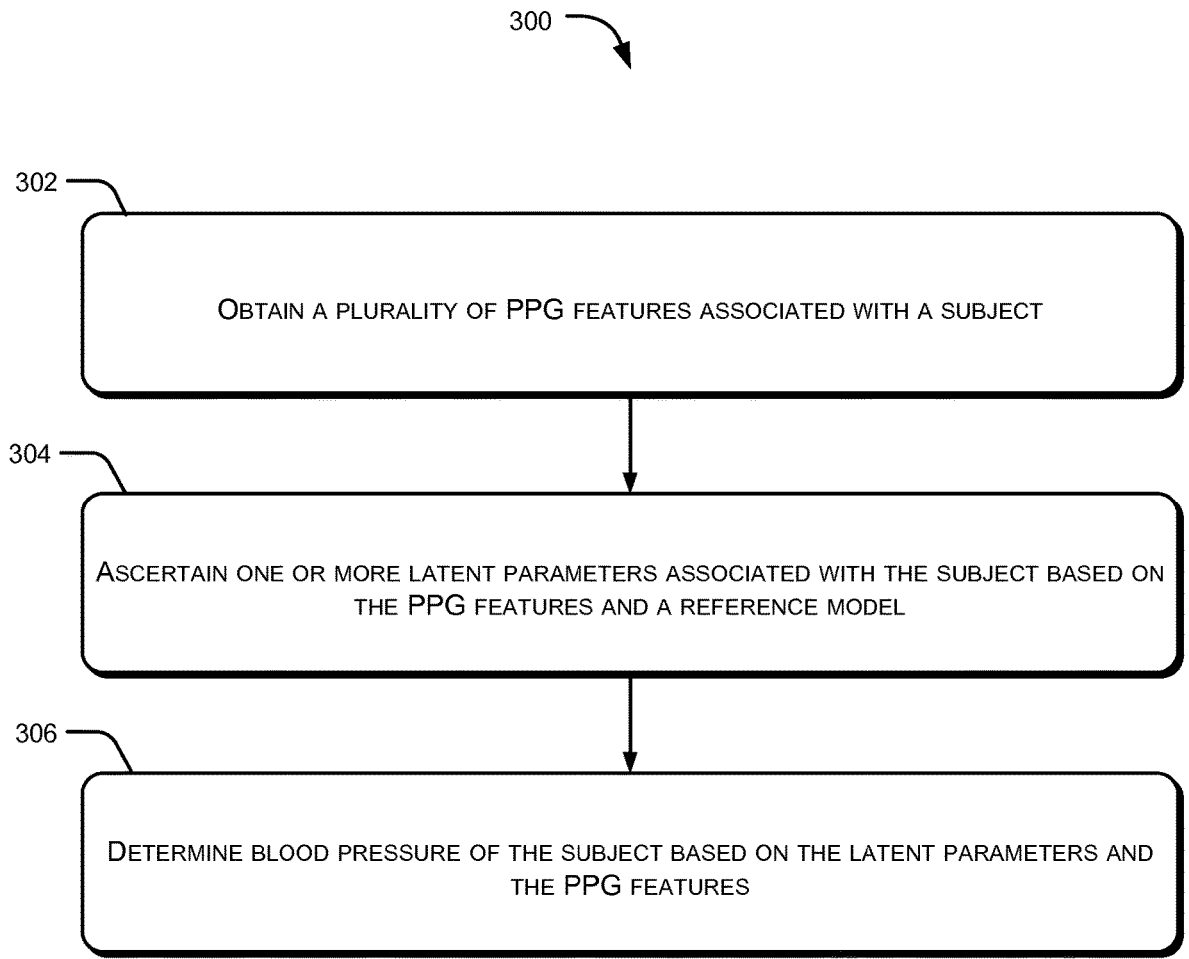
FIG. 3 illustrates a method for measuring the blood pressure of the subject, in accordance with an implementation of the present subject matter.

FIG. 2 illustrates a method 200 for determining a reference model to measure blood pressure of a subject, and FIG. 3 illustrates a method 300 for measuring the blood pressure of the subject, according to an embodiment of the present subject matter. The order in which the methods is described is not intended to be construed as a limitation, and any number of the described methods blocks can be combined in any order to implement the methods or any alternative methods. Additionally, individual blocks may be deleted from the methods without departing from the spirit and scope of the subject matter described herein. Furthermore, the methods can be implemented in any suitable hardware, software, firmware, or combination thereof.

The methods may be described in the general context of computer executable instructions. Generally, computer executable instructions can include routines, programs, objects, components, data structures, procedures, modules, functions, etc., that perform particular functions or implement particular abstract data types. The methods may also be practiced in a distributed computing environment where functions are performed by remote processing devices that are linked through a communications network. In a distributed computing environment, computer executable instructions may be located in both local and remote computer storage media, including memory storage devices.

In an implementation, one or more of the methods described herein may be implemented at least in part as instructions embodied in a non-transitory computer-readable medium and executable by one or more computing devices. In general, a processor, for example, a microprocessor, receives instructions from a non-transitory computer-readable medium, for example, a memory, and executes those instructions, thereby performing one or more methods, including one or more of the methods described herein. Such instructions may be stored and/or transmitted using any of a variety of known computer-readable media.

With reference to the description of FIG. 2 and FIG. 3, for the sake of brevity, the details of the components of the modeling system 102 and the device 104 are not discussed here. Such details can be understood as provided in the description provided with reference to FIG. 1.

Referring to FIG. 2, at block 202, a sample dataset comprising physiological data associated with each of a plurality of test subjects is obtained. In an example, the physiological data may comprise a PPG waveform associated with a test subject and at least one ground truth value of blood pressure of the test subject. The ground truth value may be understood as a value of blood pressure measured using a conventional sphygmomanometer device. Examples of the ground truth value may include, but are not limited to, a maximum value of the blood pressure, i.e., systolic blood pressure, and a minimum value of the blood pressure, i.e., diastolic blood pressure.

At block 204, for each of the plurality of test subjects, the physiological data associated with the test subject is processed to obtain a plurality of PPG features. Example, of the PPG features may include, but are not limited to, a systolic upstroke time period ($T_s$), a diastolic time period ($T_d$), and a sum (B) of systolic width and diastolic width determined, based on the PPG waveform, at predetermined intervals. In an example, a distance between a trough and an immediate peak point may be ascertained to be the $T_s$. In another example, a distance between a peak point and an immediate trough may be ascertained to be the $T_d$.

At block 206, for each of the plurality of test subjects, one or more latent parameters associated with the test subject are computed based at least on the plurality of PPG features. In an example, the latent parameters may be computed based on the PPG features and the ground truth value of the blood pressure of the individual. In said example, the latent parameters may be computed using the equations 1(a) and 1(b) as illustrated in FIG. 1 above.

At block 208, based on the plurality of PPG features and the one or more latent parameters associated with each of the plurality of test subjects, a reference model for determining blood pressure of a subject is determined. In an example, the PPG features and the latent parameters of each of the test subjects may be correlated. Based on the correlation for each of the test subjects, the reference model may be determined. The reference model may then be deployed in devices for measuring the blood pressure of the subject.

Further, FIG. 3 illustrates a method 300 for measuring blood pressure of a subject. Referring to FIG. 3, at block 302, a plurality of PPG features associated with a subject is obtained. In an example, the PPG features may be ascertained from a PPG waveform associated with the subject. In said example, the PPG waveform may be processed using known techniques for obtaining the PPG features. In an example, a device, such as the device 104, may obtain the features by processing the PPG waveform. In another example, the device may obtain the PPG features through a user input.

At block 304, one or more latent parameters associated with the subject are ascertained based on the PPG features and a reference model. In an example, the reference model may indicate a correlation between the PPG features and the latent parameters. In said example, the reference model may be determined based on physiological data associated with a plurality of test subjects. In an example, the PPG features of the subject may be compared with the PPG features included in the reference model, and in case of a successful match, the latent parameters corresponding to the PPG features of the reference model may be identified to be the latent parameters of the subject. In another example, the latent parameters may be ascertained based on the reference model and the PPG features using machine learning techniques.

At block 306, blood pressure of the subject is determined based on the latent parameters and the PPG features. In an example, a systolic blood pressure ($P_s$) and a diastolic blood pressure ($P_d$) of the subject may be determined based on the latent parameters and the PPG features using the equations 1(a) and 1(b) as illustrated in FIG. 1 above.

Although implementations for methods and systems for measuring blood pressure of a subject are described, it is to be understood that the present subject matter is not necessarily limited to the specific features or methods described. Rather, the specific features and methods are disclosed as implementations for measuring blood pressure of a subject.

We claim:

1. A device for measuring blood pressure of a present subject, the device comprising:
   a processor; and
   one or more memories coupled to the processor,
   wherein the processor is capable of executing programmed instructions stored in the one or more memories to:
   obtain a first plurality of photoplethysmogram (PPG) features from a PPG waveform associated with the present subject, wherein the first plurality of PPG features include a systolic upstroke time period ($T_s$), a diastolic time period ($T_d$), and a sum of a systolic width and a diastolic width determined based on the PPG waveform at a predetermined interval, and wherein the sum of the systolic width and the diastolic width is computed at a predefined percent of a peak amplitude of the PPG waveform;
   identify the systolic upstroke time period ($T_s$) upon determining a time difference between a first trough and a first peak point immediate to the first trough in the PPG waveform;
   identify the diastolic time period ($T_d$) upon determining a time difference between a second peak point and a second trough immediate to the second peak point in the PPG waveform;

ascertain one or more latent parameter values associated with the present subject based on comparison of the first plurality of PPG features to a reference model,
    wherein the reference model indicates a correlation between a second plurality of PPG features of a plurality of test subjects and one or more latent parameter values associated with the plurality of test subjects,
    wherein the one or more latent parameter values of the plurality of test subjects include arterial compliance and peripheral resistance,
    wherein the ascertainment identifies a match between the first plurality of PPG features of the present subject to the second plurality of PPG features of the plurality of test subjects based on comparison of the first plurality of PPG features of the present subject to the second plurality of PPG features of the plurality of test subjects, and
    wherein the ascertainment designates the one or more latent parameter values of the plurality of the test subjects corresponding to the matching second plurality of PPG features as the one or more latent parameter values associated with the present subject; and
  determine the blood pressure of the present subject, in real-time, based on both the obtained first plurality of PPG features associated with the present subject and the ascertained one or more latent parameter values of the present subject that were ascertained based on the obtained first plurality of PPG features associated with the present subject.

2. The device of claim 1, wherein a BPM module of the device analyzes the PPG waveform associated with the present subject to obtain the first plurality of PPG features.

3. The device of claim 2, wherein the obtaining of the first plurality of PPG features includes extracting each PPG feature of the first plurality of PPG features in one of a time domain and a frequency domain.

4. A processor-implemented method for measuring blood pressure of a present subject, the method comprising:
  obtaining a first plurality of photoplethysmogram (PPG) features from a PPG waveform associated with the present subject, wherein the first plurality of PPG features include a systolic upstroke time period ($T_s$), a diastolic time period ($T_d$), and a sum of a systolic width and a diastolic width determined based on the PPG waveform at a predetermined interval, and wherein the sum of the systolic width and the diastolic width is computed at a predefined percent of a peak amplitude of the PPG waveform;
  identifying the systolic upstroke time period ($T_s$) upon determining a time difference between a first trough and a first peak point immediate to the first trough in the PPG waveform;
  identifying the diastolic time period ($T_d$) upon determining a time difference between a second peak point and a second trough immediate to the second peak point in the PPG waveform;
  ascertaining one or more latent parameter values associated with the present subject based on comparison of the first plurality of PPG features to a reference model, and
  wherein the reference model indicates a correlation between a second plurality of PPG features of a plurality of test subjects and one or more latent parameter values associated with the plurality of test subjects,
  wherein the one or more latent parameter values of the plurality of test subjects include arterial compliance and peripheral resistance,
  wherein the ascertainment identifies a match between the first plurality of PPG features of the present subject to the second plurality of PPG features of the plurality of test subjects based on comparison of the first plurality of PPG features of the present subject to the second plurality of PPG features of the plurality of test subjects, and
  wherein the ascertainment designates the one or more latent parameter values of the plurality of the test subjects corresponding to the matching second plurality of PPG features as the one or more latent parameter values associated with the present subject;
  and
  determining the blood pressure of the present subject in real-time, based on both the obtained first plurality of PPG features associated with the present subject and the ascertained one or more latent parameter values of the present subject that were ascertained based on the obtained first plurality of PPG features associated with the present subject.

5. The method of claim 4, wherein the obtaining of the first plurality of PPG features includes extracting each PPG feature of the first plurality of PPG features in one of a time domain and a frequency domain.

6. A non-transitory computer readable medium including a computer program for executing a method for measuring blood pressure of a present subject, the method comprising:
  obtaining a first plurality of photoplethysmogram (PPG) features from a PPG waveform associated with the present subject, wherein the first plurality of PPG features include a systolic upstroke time period ($T_s$), a diastolic time period ($T_d$), and a sum of a systolic width and a diastolic width determined based on the PPG waveform at a predetermined interval, and wherein the sum of the systolic width and the diastolic width is computed at a predefined percent of a peak amplitude of the PPG waveform;
  identifying the systolic upstroke time period ($T_s$) upon determining a time difference between a first trough and a first peak point immediate to the first trough in the PPG waveform;
  identifying the diastolic time period ($T_d$) upon determining a time difference between a second peak point and a second trough immediate to the second peak point in the PPG waveform;
  ascertaining one or more latent parameter values associated with the present subject based on comparison of the first plurality of PPG features to a reference model,
  wherein the reference model indicates a correlation between a second plurality of PPG features of a plurality of test subjects and one or more latent parameter values associated with the plurality of test subjects,
  wherein the one or more latent parameter values of the plurality of test subjects include arterial compliance and peripheral resistance,
  wherein the ascertainment identifies a match between the first plurality of PPG features of the present subject to the second plurality of PPG features of the plurality of test subjects based on comparison of the first plurality of PPG features of the present subject to the second plurality of PPG features of the plurality of test subjects, wherein the ascertainment designates the one or more latent parameter values of the plurality of the test subjects corresponding to the matching second plurality of PPG features as the one or more latent parameter values associated with the present subject; and determining the blood pressure of the present subject in real-time, based on both the obtained first plurality of PPG features associated with the present subject and the ascertained one or more latent parameter values of the present subject that were also ascertained based on the obtained first plurality of PPG features associated with the present subject.

7. The non-transitory computer readable medium of claim 6, wherein the obtaining of the first plurality of PPG features includes extracting each PPG feature of the first plurality of PPG features in one of a time domain and a frequency domain.

* * * * *